(12) United States Patent
Kaouas et al.

(10) Patent No.: US 8,815,321 B2
(45) Date of Patent: Aug. 26, 2014

(54) GERANYLAMINE DERIVATIVES AS FLAVOURING AGENTS

(75) Inventors: Abdelmajid Kaouas, Utrecht (NL); Harry Renes, Lelystad (NL); Cornelis Winkel, Bussum (NL)

(73) Assignee: Givaudan S.A., Vernier (CH)

( * ) Notice: Subject to any disclaimer, the term of this patent is extended or adjusted under 35 U.S.C. 154(b) by 495 days.

(21) Appl. No.: 13/202,194

(22) PCT Filed: Feb. 16, 2010

(86) PCT No.: PCT/EP2010/051911
§ 371 (c)(1),
(2), (4) Date: Sep. 23, 2011

(87) PCT Pub. No.: WO2010/094679
PCT Pub. Date: Aug. 26, 2010

(65) Prior Publication Data
US 2012/0015089 A1    Jan. 19, 2012

(30) Foreign Application Priority Data

Feb. 19, 2009  (GB) .................................. 0902849.9

(51) Int. Cl.
| A23L 1/226 | (2006.01) |
| A23L 2/56 | (2006.01) |
| C07C 235/06 | (2006.01) |

(52) U.S. Cl.
CPC ............. *A23L 1/226* (2013.01); *C07C 235/06* (2013.01); *A23L 2/56* (2013.01); *A23L 1/22614* (2013.01)
USPC .......................................... 426/534; 564/203

(58) Field of Classification Search
USPC ....................................................... 426/534
See application file for complete search history.

(56) References Cited

U.S. PATENT DOCUMENTS

| 7,125,852 | B2 | 10/2006 | Akiyama |
| 7,427,421 | B2 | 9/2008 | Dewis et al. |
| 7,507,765 | B2 | 3/2009 | Akiyama |
| 7,794,768 | B2 | 9/2010 | Dewis et al. |
| 7,919,133 | B2 | 4/2011 | Looft et al. |
| 2005/0119474 | A1 | 6/2005 | Akiyama |
| 2006/0057268 | A1 | 3/2006 | Dewis et al. |
| 2006/0142244 | A1 | 6/2006 | Akiyama |
| 2007/0134389 | A1 | 6/2007 | Pei et al. |
| 2008/0199584 | A1* | 8/2008 | Kaouas et al. ................ 426/535 |
| 2008/0292763 | A1 | 11/2008 | Looft et al. |
| 2008/0317922 | A1 | 12/2008 | Dewis et al. |

FOREIGN PATENT DOCUMENTS

| DE | 10 2006 006 123 A1 | 9/2006 |
| EP | 1 471 052 A1 | 10/2004 |
| EP | 1 642 886 A2 | 4/2006 |
| EP | 1 989 944 B1 | 6/2010 |

OTHER PUBLICATIONS

GB 0902849.9-Great Britain Search Report, May 12, 2009.
PCT/CH2010/051911-Written Opinion of the International Searching Authority, Aug. 4, 2010.
PCT/CH2010/051911-International Search Report, Aug. 4, 2010.
Akiyama, Kiyoshi, et al., "Antitumor Effect of Geranylamine Derivatives on Human Hepatoma", In Vivo, 2005 vol. 19, pp. 173-178, XP-002590327.

* cited by examiner

Primary Examiner — Humera Sheikh
Assistant Examiner — Jeffrey Mornhinweg
(74) Attorney, Agent, or Firm — Curatolo Sidoti Co., LPA; Joseph G. Curatolo; Salvatore A. Sidoti

(57) ABSTRACT

Compounds of the formula (I)

A is OH or a carbonyl group,
n is 0 or 1,
R is an alkyl radical having from 1 to 4 carbon atoms, in particular methyl, ethyl, n-propyl, iso-propyl, n-butyl or t-butyl; or a residue of a hydroxy carboxylic acid, in particular the residue —CH(OH)COOH, —CH(OH)CH$_2$COOH, —CH$_2$CH(OH)COOH or —CH(OH)CH(OH)COOH; and
R' is independently selected from H or OH.

6 Claims, No Drawings

GERANYLAMINE DERIVATIVES AS FLAVOURING AGENTS

CROSS REFERENCE TO RELATED APPLICATIONS

This application is a national stage application of International Application No. PCT/EP2010/051911, filed 16 Feb. 2010, which claims priority from Great Britain Patent Application Serial No. 0902849.9, filed 19 Feb. 2009, from which applications priority is claimed, and which are incorporated herein by reference.

The present invention is concerned with organic compounds and their use as flavouring substances, in particular their use in creating, modifying or enhancing taste, in particular umami-taste.

It is widely regarded that the flavour of a foodstuff consists of two parts, namely its aroma and its taste. In general, what is perceived olfactively in the nasal cavity is considered to be an aroma, whereas the term "taste" is used to describe a sensorial impact perceived in the mouth, and more particularly the tongue. There are five generally recognised taste sensations: Sweet, bitter, sour, salt and umami.

Umami is now generally recognised as the 5th basic taste property, indeed receptors for umami have been discovered in taste buds on the tongue. Umami has qualities that differentiate it from the other known taste sensations. The most common descriptors for umami are "savoury", "meaty" and "broth-like". Umami contributes to the flavour of foodstuffs, particularly in the savoury range.

By far the most used material to impart an umami-taste is mono-sodium glutamate (MSG). MSG is used in practically all savoury industrial products to improve taste quality. However, although there is no scientific evidence supporting the theory, it is perceived by the public as being unhealthy. For this reason, work continues on the discovery of new strongly tasting umami molecules.

Flavour molecules that contain amide functionality have been known for a long time. Alkamides such as spilanthol and shanshool are known to create a prickling, tingling effect in the mouth. The same tingling, prickling sensation is characteristic of the unsaturated N-alkylamide-pellitorin. Structural modifications of pellitorin were described in DE 102006006123, however none were found to be umami-tasting.

Umami-tasting molecules have been described in EP1642886 and also in EP1989944. There remains a need to provide improved compounds that create, enhance or modify taste, in particular umami-taste, in consumable products.

The invention provides in a first aspect a compound of the formula (I)

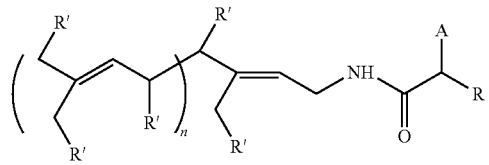

wherein A is OH or a carbonyl group,
n is 0 or 1,
R is an alkyl radical having from 1 to 4 carbon atoms, in particular methyl, ethyl, n-propyl, iso-propyl, n-butyl or t-butyl; or a residue of a hydroxy carboxylic acid, in particular the residue —CH(OH)COOH, —CH(OH)CH$_2$COOH, —CH$_2$CH(OH)COOH or —CH(OH)CH(OH)COOH; and R' is independently selected from H or OH.

Preferred compounds of the formula (I) are geranyl lactamide (that is, the compound wherein n=1, A=OH, R=methyl and R' is H); and n-prenyl lactamide (that is, the compound wherein n=0, A=OH, R=methyl, and R' is H).

The present invention further relates to a method for preparing a compound of formula (I). The skilled person will immediately appreciate that the preparation of compounds of formula (I) can be achieved using straightforward synthetic procedures and readily available starting materials.

By way of illustration, compounds of formula (I) may be prepared by the reaction of an amine, such as the geranyl or n-prenyl amine with an ester, acid chloride or anhydride containing appropriate A and R substituents. Having regard to the nature of the substituents A and R, they may need to be protected during this reaction with appropriate protecting groups, particularly when it is an acid chloride or an anhydride that is reacted with the amine. Suitable protecting groups include tetrahydropyranyl (THP) or simple aliphatic ester groups.

The reaction conditions, that is, the choice of solvent, temperature, pH and the like, appropriate for affecting the chemical syntheses described above are well known in the art and require no further elaboration here. Particular reaction conditions are set forth in the examples below.

We have surprisingly found that compounds of the formula (I) can create, modify or enhance taste of consumable products to which they are added. In particular, compounds of formula (I) may create, enhance or modify umami-taste in consumable products.

By consumable products is meant products, such as beverages and foodstuffs, or personal care products that are intended to be introduced into the oral cavity of a human or animal and remain there for a certain period of time before being ingested or removed from the mouth. Such compositions include compositions in their processed, partially processed or unprocessed state. They include materials that are added to food in their preparation, processing or handling. Particular consumable products wherein compounds of formula (I) may find use are savoury products, such as soups, beverages, snack foods such as potato chips, pizza, fast foods and the like.

The compounds of formula (I) may also be used in reduced MSG or MSG-free consumer products as well as those containing the substance in customary amounts. MSG is customarily employed in consumable products in amounts of 200 to 500 ppm. Reduced MSG consumer products accordingly contain amounts lower amounts, such as 100 ppm to 200 ppm.

Accordingly, the invention provides in another of its aspects the use of a compound of the formula (I) as defined hereinabove for creating, enhancing or modifying taste, particularly an umami-taste, in consumable products.

Another aspect of the invention concerns flavour compositions comprising or consisting of an effective amount of a compound of formula (I).

An effective amount may range from about 0.001% to 100% of the total weight of the flavour composition. What constitutes an effective amount depends largely on the nature of the consumable product to which it is desired to add, modify or create flavour and the particular sensorial effect that is desired to be achieved for that consumable product. Typically, consumer products will contain from about 5 ppm to 50 ppm of a compound of the formula (I).

Flavour compositions of the present invention may contain in addition to a compound of the formula (I) other flavour ingredients that will modify, enhance or create flavour in a consumer product that is to be flavoured.

In addition to additional flavour ingredients, a flavour composition may contain other ingredients useful as excipients such as carriers, diluents or bulking agents or the like, the purpose of which is to aid in the processing of a flavour composition or consumer product containing same, or otherwise impart a desirable property on the composition or consumer product. Examples of such ingredients may include carbohydrates and carbohydrate polymers, e.g. polysaccharides, cyclodextrines, starches, starch hydrolysates, modified starches, modified celluloses, gums such as gum arabic, ghatti gum, traganth, karaya, carrageenan, guar, locust bean, alginates, pectin, inulin, or xanthan.

There now follows a series of examples that serve to illustrate the invention:

EXAMPLE 1

Preparation of Geranyl Lactamide

Method 1: Reaction of Geranyl Amine with the Lactate Ester 2 g of geranylamine was added to a solution of 1.4 g of ethyl lactate in 15 ml of ethanol at room temperature. The reaction mixture was stirred at reflux for 5 hours. Then the solvent was removed on rotary evaporator to yield 2.8 g of pale yellow oil. The purity was approximately 90% according to NMR analysis. The crude product was purified by flash column chromatography (silica gel, ethyl acetate:pentane 7:3) to give quite pure geranyl lactamide according to NMR and TLC analysis.

$^1$H-NMR in $CDCl_3$: 1.65-1.75 (9H, 2×s, 3×CH3-C=C), 2.0 (4H, m, 2×CH2-CH=C), 3.8 (2H, m, CH2-NH), 5.2 (1H, t, CH—CH2-CH2), 5.3 (1H, t, CH—CH2-NH), 9 (1H, s, NH), 1.4 (3H, s, CH3-CHOH—CO), 4.1 (1H, s, OH), 4.3 (1H, q, —CHOH—CH3)

Method 2: Reaction of Geranyl Amine with Acid Chloride

Step 1: Preparation of the intermediate N-geranyl 2-acetoxypropionamide

To a cold solution of geranyl amine (7 g) and triethyl amine (6 g) in THF (50 ml) was added dropwise a solution of 2-acetoxypropanoyl chloride (9 g) in dichloromethane (15 ml) at a temperature between 6° C. and 13° C. over a period of 20 minutes. Stirring was continued at room temperature for 2 hrs. The white precipitate (triethylamine HCl salt) was filtered and the filtrate was evaporated. The residue was dissolved in DCM (100 ml), washed twice with 50 ml of aqueous 5% HCl solution and twice with water (2×50 ml) and evaporated to dryness to yield 12.6 g of a colourless oil. The yield was 90%, the purity was 95% according to NMR analysis.

Step 2: Hydrolysis of N-geranyl 2-acetoxypropionamide

A solution of N-geranyl 2-acetoxypropionamide (10 g) in THF (15 ml) was added to a cold aqueous 10% NaOH solution (60 g). The resultant mixture was stirred at temperature between 5 and 10° C. for 2 hrs. Then the mixture was acidified to pH 1-2 and extracted twice with dichloromethane (2×100 ml). The organic phases were combined and washed twice with water (2×50 ml) and evaporated to dryness. The yield was 6 g of colourless oil. The purity was 80% according to NMR.

$^1$H-NMR in $CDCl_3$: 1.65-1.75 (9H, 2×s, 3×CH3-C=C), 2.0 (4H, m, 2×CH2-CH=C), 3.8 (2H, m, CH2-NH), 5.2 (1H, t, CH—CH2-CH2), 5.3 (1H, t, CH—CH2-NH), 9 (1H, s, NH), 1.4 (C3H, s, CH3-CHOH—CON), 4.1 (1H, s, OH), 4.3 (1H, q, —CHOH—CH3)

Preparation of N-prenyl lactamide

A mixture of ethyl lacate (2 g) and 3-methyl-2-buten-1-amine (2 g) was stirred for 1 hour at 90° C. and 1 hour at 120° C. During the reaction the formed ethanol was distilled off. The unreacted starting materials were removed under reduced pressure and the crude product was purified by Kugelrhor distillation. 2 g of colourless oil was obtained. The product was pure according to NMR analysis. The yield was 75%.

$^1$H-NMR in $CDCl_3$: 1.7 (6H, s, 2×CH3-C=C), 3.8 (2H, d, CH2-N), 5.3 (1H, t, olefinic CH—CH2), 9.0 (1H, s, NH), 1.4 (3H, s, CH3-CHOH—COO), 4.1 (1H, s, OH), 4.3 (1H, q, —CHOH—CH3)

EXAMPLE 2

Two solutions were prepared:
A a solution of 0.3% NaCl
B a solution of 0.3% NaCl and 10 ppm geranyl lactamide
The samples were tasted by a trained sensory panel composed of 20 women aged between 30 and 60. The findings of the panel were summarized as:
Solution A: salty
Solution B: salty, umami

EXAMPLE 3

Two solutions were prepared:
A a solution of 0.3% NaCl and 0.03% MSG
B a solution of 0.3% NaCl, 0.03% MSG and 10 ppm geranyl lactamide
The samples were tasted by a trained sensory panel composed of 20 women aged between 30 and 60. The findings of the panel were summarized as:
Solution A: salty, umami
Solution B: salty, umami, more bouillon-like, more complex, less sweet.

EXAMPLE 4

A tomato soup mix was prepared from 9.4 g of sodium chloride, 1 g of mono sodium glutamate, 0.08 g ribonucleotides (ex yeast), 32 g of tomato powder (ex Spreda), 25.1 g of glucose, 21 g of starch (Ultrasperse 5 ex National Starch), 5 g of palm fat powder, 3 g of yeast powder, 1 g of onion powder, 0.15 g of carrot powder, 0.05 g of ground white pepper, 0.3 g of celery extract powder, 0.05 g of ground laurel leaf powder, and 1.85 g of sucrose. 25 G of the well mixed ingredients was added to 250 g of boiling water and stirred until completely dissolved.

The reference soup was compared with a batch of the same soup containing 15 ppm of geranyl lactamide. A small group of flavourists (2 male, 2 female) tasted the soups and agreed that the test soup was more umami, had a long-lasting savoury aspect, was more salty and was more complex than the base soup.

EXAMPLE 5

Plain potato chips were prepared.
One part was flavoured with 1.2% sodium chloride (sample A)
One part was flavoured with 1.2% sodium chloride and 0.3% mono sodium glutamate (sample b)
One part was flavoured with 1.2% sodium chloride and 25 ppm geranyl lactamide (sample C).

The samples were tasted by a trained sensory panel composed of 20 women aged between 30 and 60.

The panel agreed that sample C was preferred over the other two samples.

Sample was described as salty, sample B as salty and umami and sample C as salty, umami, long lasting, savoury, bouillon.

EXAMPLE 6

A tomato ketchup was prepared from 19% tomato paste (28-30% dry weight), 8% of vinegar (15%), 3% of sodium chloride, 20% of sugar and 50% of water.

To one half of the batch was added 20 ppm of geranyl lactamide.

A small group of flavourists (2 male, 2 female) tasted the ketchups and agreed that the test ketchup tasted clearly more umami, more salty and had a pleasant savoury note compared with the base ketchup.

The invention claimed is:

1. A compound selected from the group consisting of geranyl lactamide and n-prenyl lactamide.
2. A flavour composition comprising the compound according to claim 1.
3. A consumable product comprising the composition according to claim 2.
4. The composition according to claim 2 wherein the composition is MSG-free.
5. A method of creating, enhancing or modifying taste of a consumer product, comprising adding a compound to the consumer product, wherein the compound is selected from the group consisting of geranyl lactamide and n-prenyl lactamide.
6. The method of claim 5 wherein the taste is an umami-taste.

* * * * *